United States Patent [19]

Renner

[11] Patent Number: 4,528,357
[45] Date of Patent: Jul. 9, 1985

[54] CURABLE MIXTURES CONTAINING HYDROXYALKYL-CYANOACETATES, AND THE USE THEREOF FOR PRODUCING CURED PRODUCTS

[75] Inventor: Alfred Renner, Muntelier, Switzerland

[73] Assignee: Ciba-Geigy Corporation, Ardsley, N.Y.

[21] Appl. No.: 635,761

[22] Filed: Jul. 30, 1984

[30] Foreign Application Priority Data

Aug. 5, 1983 [CH] Switzerland .......................... 4267/83

[51] Int. Cl.³ .............................................. C08G 59/62
[52] U.S. Cl. ...................................... 528/93; 525/504; 528/361; 528/362; 528/111
[58] Field of Search ................. 528/111, 93, 361, 362; 525/504

[56] References Cited

U.S. PATENT DOCUMENTS 4,202,920  5/1980  Renner et al. .......................... 528/93
4,283,520  8/1981  Moser et al. .......................... 427/386
4,302,573  11/1981  Stockinger et al. ............... 528/90 X

*Primary Examiner*—Earl Nielsen

*Attorney, Agent, or Firm*—Luther A. R. Hall

[57] ABSTRACT

There are described novel curable mixtures which contain (a) an epoxide resin having on average more than one epoxy group in the molecule, and
(b) as curing agent for the epoxide resin, a compound of the formula I

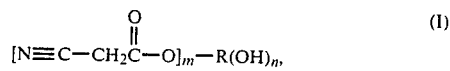

wherein m and n independently of one another are an integer from 1 to 5, and m and n together are at most 6, and R is a radical of the valency m derived from an alcohol having at most 6 hydroxyl groups, which radical can be interrupted by oxygen atoms and has a molecular weight not exceeding 200.

These mixtures are suitable for example as casting resins, impregnating resins or injection-moulding compounds.

11 Claims, No Drawings

CURABLE MIXTURES CONTAINING HYDROXYALKYL-CYANOACETATES, AND THE USE THEREOF FOR PRODUCING CURED PRODUCTS

The invention relates to curable mixtures containing hydroxyalkyl-cyanoacetates, and to the use thereof for producing cured products.

It is known that dicyanodiamide and various cyanoacetic acid derivatives, particularly cyanoacetic esters and amides, are suitable as curing agents for curable mixtures containing epoxide resins [cf. for example U.S. Pat. Nos. 4,202,920 and 4,283,520]. These prior known cyanoacetic acid derivatives are in general stable in storage; however, with regard to their reactivity as curing agents they are not completely satisfactory as yet.

Storage-stable, latent curing agents for epoxide resins having increased reactivity are obtained with the present invention.

The invention relates to curable mixtures containing:
(a) an epoxide resin having on average more than one epoxy group in the molecule, and
(b) as curing agent for the epoxide resin, a compound of the formula I $$[N\equiv C-CH_2\overset{O}{\overset{\|}{C}}-O]_m-R(OH)_n \quad (I)$$

wherein
m and n independently of one another are an integer from 1 to 5, and
m and n together are at most 6, and
R is a radical of the valency m derived from an alcohol having at most 6 hydroxyl groups, which radical can be interrupted by oxygen atoms and has a molecular weight not exceeding 200.

The compounds of the formula I are used advantageously in an amount such that there are 3 to 4 epoxy groups of component (a) to one —CH₂—CN group.

In the compounds of the formula I, m and n independently of one another are preferably 1 or 2, and m and n together are preferably 2 to 4.

Radicals R derived from alcohols having at most 6 hydroxyl groups can be straight-chain or branched-chain and, according to definition, are interrupted in each case by one or more oxygen atoms, especially by one oxygen atom. Such radicals preferably have 1–14 C atoms, in particular 2–8 C atoms and preferably 2–6 C atoms. Suitable R radicals are for example:

—(CH₂)₂—OH, —(CH₂)₃—OH, —CH₂CHCH₃, —CH₂CHCH₂—,
                                    |           |
                                    OH       OH

—(CH₂)₄OH, —CH₂CH₂CHCH₃, CH₃—CH—CH—CH₃,
                                    |           |    |
                                    OH       OH  OH

—CH₂CH—CH—CH₂—, —CH₂CH₂—O—CH₂CH₂OH,
     |    |
     OH  OH

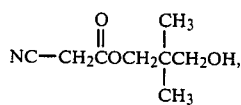

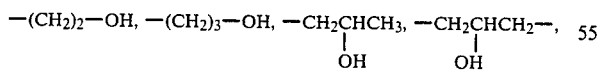

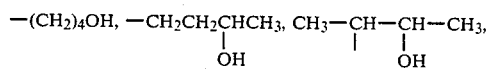

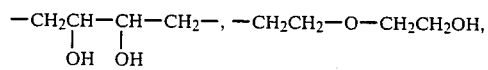

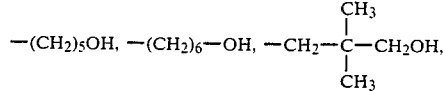

and also the radicals of arabitol, xylitol, D-sorbitol, D-mannitol and dulcitol.

There is preferably used as component (b): cyanoacetic acid-2-hydroxyethyl ester, 1,2-propylene glycol-monocyanoacetate, D-mannitol-tris-cyanoacetate or a compound of the formula

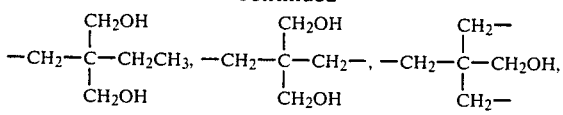

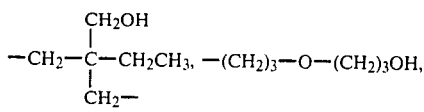

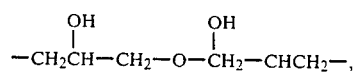

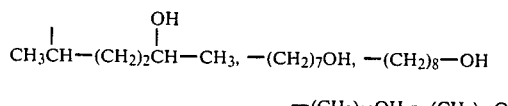

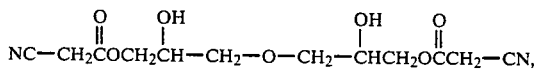

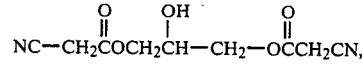

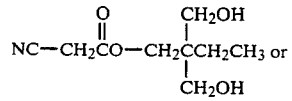

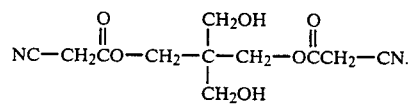

It is also possible to use mixtures of different compounds of the formula I. Particularly preferably used as component (b) is 1,2-propylene glycol-monocyanoacetate.

The compounds of the formula I are known, or they can be produced in a manner known per se, for example by azeotropic esterification of cyanoacetic acid with corresponding alcohols R(OH)ᵣ, wherein r is an integer from 1 to 6, and R has the meaning given in the foregoing. The cyanoacetic acid is used, per hydroxyl equivalent to be cyanoacetylated, in an essentially stoichiometric amount or in a slight excess, for example up to about 1.10 mols. The azeotropic esterification is performed advantageously without the addition of a catalyst but in the presence of an entrainer (separating agent) such as toluene or xylene, at a concentration of 25–50%. Practically acid-free solutions of the compounds of the formula I are in general obtained by this process. When the acid number of the product obtained is more than 10 mg KOH/g, the reaction solution is advantageously extracted with a base, for example with an aqueous solution of sodium hydrogen carbonate.

Suitable epoxide resins (a) for the curable mixtures according to the invention are in particular liquid epoxide resins, especially liquid aliphatic, aromatic or heterocyclic polyepoxides. Preferred polyepoxides are those based on polyhydric phenols, particularly dihydric phenols, such as 2,2-bis(4-hydroxyphenyl)propane(bisphenol A), 2,2-bis(3,5-dibromo-4-hydroxyphenyl)-propane(tetrabromo-bisphenol A) or 4,4'-dihydroxydiphenylmethane(bisphenol F); polyepoxides based on novolaks, especially phenol-formaldehyde or cresol-formaldehyde novolaks; polyepoxides based on polyhydric aliphatic alcohols, in particular diols having 2–6 C atoms, such as 1,4-butanediol; polyepoxides based on aromatic mono- or polyamines, such as aminophenols, for example triglycidyl-p-aminophenol, and N,N,N',N'-tetraglycidyl-4,4'-diaminodiphenylmethane. Also mixtures of different polyepoxides can be used. Particularly preferred are liquid, unmodified epoxide resins based on bisphenol F and especially on bisphenol A, for example having an epoxide content of 5.1 to 5.7 equivalents/kg and a viscosity of about 7.5 to 12.0 Pas at 25° C.

The mixtures according to the invention preferably contain in addition 0.1 to 10 parts by weight, relative to 100 parts by weight of epoxide resin (a), of a curing accelerator (c). Suitable curing accelerators (c) are in particular compounds of the formula II

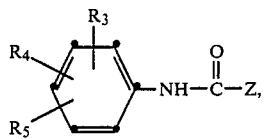

(II)

wherein Z is the group

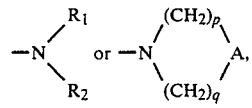

wherein A is —CH$_2$— or —NH—, p is zero, 1 or 2, and q is 1 or 2, and R$_1$ and R$_2$ independently of one another are each an alkyl group having 1–4 C atoms, R$_3$ and R$_4$ independently of one another are each hydrogen, halogen, alkyl having 1–4 C atoms, alkoxy having 1–4 C atoms, phenyl or phenoxy, and R$_5$ is hydrogen, trifluoromethyl, nitro or any one of the groups

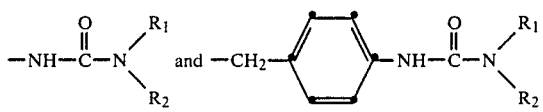

Further suitable curing agents (c) are imidazoles, such as 2-methylimidazole, 2-ethyl-4-methylimidazole, 2-phenylimidazole and especially 1-methyl- or 1-ethylimidazole.

Curing accelerators (c) preferably used are the compounds of the formula II in which Z is the group —N(R$_1$)(R$_2$), R$_1$ and R$_2$ independently of one another are each methyl or ethyl, R$_3$ and R$_4$ independently of one another are each hydrogen, halogen, alkyl or alkoxy having 1–4 carbon atoms, and R$_5$ is hydrogen or trifluoromethyl. Particularly preferred is N-(4-trifluoromethylphenyl)-N',N'-dimethylurea, and more particularly preferred are N-(4-chlorophenyl)-N',N'-dimethylurea(=monuron) and N-(4-ethoxyphenyl)-N',N'-dimethylurea. The curing accelerator is preferably added in an amount of 0.1 to 5 parts by weight, relative to 100 parts by weight of the epoxide resin (a).

To effect an improvement of specific mechanical and/or thermal properties of the cured products, for example the impact strength, the heat deflection temperature and/or the resistance to boiling water, there can be advantageously added to the mixtures according to the invention also modifiers, particularly polyvalent isocyanates, especially diisocyanates. By virtue of their bifunctionality, the curing agents (b) as defined can be reacted both with epoxides and with isocyanates. The cyanoacetyl groups of the curing agent of the formula I react principally with the epoxide resin, whereas the hydroxyl groups thereof react mainly with the isocyanate. Suitable polyvalent isocyanates are in particular aliphatic, cycloaliphatic, araliphatic and aromatic di- or triisocyanates. Examples of suitable di- and triisocyanates are: compounds of the formula OCN—C$_a$H$_{2a}$—NCO wherein a=4 to 9, such as tetramethylene- and hexamethylenediisocyanate, isomeric mixtures of 2,2,4- and 2,4,4-trimethylhexamethylenediisocyanate; 3-isocyanatomethyl-3,5,5-trimethyl-cyclohexylisocyanate(isophoronediisocyanate); m- and p-xylylenediisocyanate; aromatic di- or triisocyanates, which can be substituted on the aromatic nuclei by C$_1$–C$_4$-alkyl groups, particularly methyl groups, such as m- and p-phenylenediisocyanate, naphthalenediisocyanate, 4,4'-diphenylmethanediisocyanate, 2,4- and 2,6-tolylenediisocyanate and triphenylmethanetriisocyanate. Preferably used are hexamethylenediisocyanate, 4,4'-diphenylmethanediisocyanate and mixtures of 2,4- and 2,6-tolylenediisocyanate. The isocyanates are advantageously used in an amount such that the ratio of the OH groups in the compounds of the formula I to the isocyanate groups is about 1:1.

The mixtures according to the invention can be produced by simply bringing the components together and gently heating them until they have dissolved. In the case of a solid epoxide resin, this is heated until melted, whereupon the curing agent and optionally the curing accelerator and/or modifier are dissolved therein.

To the mixtures according to the invention can also be added: extenders, reinforcing agents, pigments, fillers and other additives customarily used for specific purposes, such as minerals, wood flour, glass fibres, carbon fibres or boron fibres, polyamides, polyesters, carbon black and metal oxides.

The mixtures can be used in the most varied technical fields, for example as casting resins (also filled with minerals), for example for the so-called pressure-gellation process, as injection-moulding compounds, dripping resins, laminating resins, adhesives, formulations for surface coatings or as lacquer components. They are preferably used as casting resins, dripping resins or injection moulding compounds. The mixtures according to the invention in general gel at temperatures of between 80° and 120° C. Cured products can be produced by heating the mixtures to a temperature above 120° C., preferably between 120° and 200° C.

The curable mixtures according to the invention are distinguished by a low viscosity and in particular by shortened gelling and curing times. This is surprising since it was not to be expected that hydroxyl groups would have an accelerating effect on the known curing of epoxide resins by way of cyanacetyl groups.

The term 'parts' in the following Examples denotes parts by weight.

PRODUCTION EXAMPLES 1-8

Example 1

1.05 mols of cyanoacetic acid are esterified in a 30-50% toluene solution at boiling temperature, with azeotropic water separation, with 1 mol of ethylene glycol. After completion of the azeotropic water separation, the azeotropic distillation is continued for a further 3 hours, whilst the returning toluene is passed through granulated soda lime as dehydrating agent. Practically acid-free solutions of hydroxyalkylcyanoacetic ester are in general obtained in this manner. If the acid number of the product obtained is more than 10 mg/KOH/g, the reaction solution is extracted with a 5% NaHCO$_3$ solution. On removal of the toluene in a rotary evaporator at 140° C./2 kPa, there is thus obtained cyanoacetic acid-2-hydroxyethyl ester in a yield of 46.4% of theory; b.p. 140° C./1.6 Pa, $n_{20}{}^D$=1.4531; viscosity at 20° C. ($\eta_{20}$)=64 mPas.

Elementary analysis: calculated: C 46.51%, H 5.46%, N 10.85%, found: C 46.23%, H 5.46%, N 10.90%.

EXAMPLE 2

In a manner analogous to that described in Example 1, 1.05 mols of cyanoacetic acid are esterified with 1 mol of 1,2-propanediol. 1,2-Propylene glycolmonocyanoacetate is obtained in a yield of 47.0% of theory; b.p. 127° C./9.3 Pa, $n_{20}{}^D$=1.4498; $\eta_{20}$=504 mPas.

Elementary analysis: calculated: C 50.35%, H 6.34%, N 9.79%, found: C 50.16%, H 6.25%, N 10.22%.

EXAMPLE 3

In a manner analogous to that described in Example 1, 2.10 mols of cyanoacetic acid are esterified with 1 mol of glycerol. The glycerol-bis-cyanoacetate of the formula

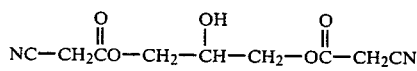

is obtained in a yield of 94.1% of theory (not distillable); $n_{20}{}^D$=1.4774; $\eta_{20}$=80,000 mPas.

Elementary analysis: calculated: C 47.79%, H 4.46%, N 12.39%, found: C 47.05%, H 4.65%, N 12.15%.

EXAMPLE 4

In a manner analogous to that described in Example 1, 2.10 mols of cyanoacetic acid are esterified with 1 mol of diglycerol [HO—CH$_2$CH(OH)CH$_2$OCH$_2$CH(OH)CH$_2$—OH]. There is obtained the compound of the formula

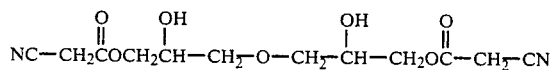

in a yield of 95.6% of theory (not distillable); $n_{20}{}^D$=1.4830, $\eta_{20}$=60,000 mPas.

Elementary analysis: calculated: C 48.00%, H 5.37%, N 9.33%, found: C 47.77%, H 5.49%, N 9.09%.

EXAMPLE 5

In a manner analogous to that described in Example 1, 1.05 mols of cyanoacetic acid are esterified with 1 mol of 1,1,1-trimethylolpropane[2-ethyl-2-(hydroxymethyl)-1,3-propanediol]. There is obtained a light-yellow liquid resin which corresponds largely to the formula

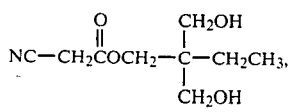

in a yield of 95.3% of theory (not distillable); $n_{20}{}^D$=1.4791, $\eta_{20}$=29,100 mPas.

Elementary analysis: calculated: C 53.72%, H 7.51%, N 6.96%, forund: C 53.91%, H 7.51%, N 6.85%.

EXAMPLE 6

In a manner analogous to that described in Example 1, 2.10 mols of cyanoacetic acid are esterified with 1 mol of 1,1,1-trimethylolpropane. There is obtained a tough yellow resin corresponding to the formula

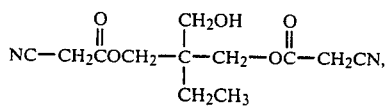

in a yield of 95.4% of theory (not distillable); $n_{20}{}^D$=1.4793, $\eta_{20}$=72,800 mPas.

Elementary analysis: calculated: C 53.73%, H 6.01%, N 10.44%, found: C 53.5%, H 6.1%, N 10.4%,

EXAMPLE 7

In a manner analogous to that described in Example 1, 2.10 mols of cyanoacetic acid are esterified with 1 mol of pentaerythritol. There is obtained a resin almost solid at room temperature, corresponding to the formula

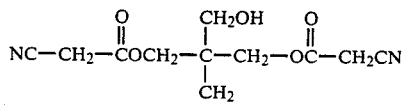

in a yield of 93.6% of theory; $\eta_{80}$=36,200 mPas.

Elementary analysis: calculated: C 48.89%, H 5.22%, N 10.37%, found: C 48.53%, H 5.36%, N 10.15%.

EXAMPLE 8

In a manner analogous to that described in Example 1, 3.15 mols of cyanoacetic acid are esterified with 1 mol of D-mannitol. The D-mannitol-tris-cyanoacetate is obtained in a yield of 90.6% of theory and in the form of a resin-like, semisolid substance; $\eta_{80}$=28,400 mPas.

Elementary analysis: calculated: C 47.00%, H 4.47%, N 10.96%, found: C 46.62%, H 4.98%, N 10.22%.

APPLICATION EXAMPLES I–VIII

EXAMPLE I

A mixture is produced from 100 parts of a liquid condensation product, prepared in the presence of sodium hydroxide and consisting of bisphenol-A and epichlorohydrin, having an epoxide equivalent weight of 175.4 (5.7 equivalents/kg; resin I), 17.22 parts of cyanoacetic acid-2-hydroxyethyl ester and 2.344 parts of N-(4-chlorophenyl)-N',N'-dimethylurea as the accelerator; and the mixture is poured into a plate mould having dimensions of 150×150×4 mm$^3$. The mixture is subsequently gelled for 4 hours at 100° C., and is then cured for 6 hours at 140° C. and for 6 hours at 180° C. There is obtained a perfectly satisfactory, tough and hard plate, from which are cut test specimens having the following properties:

| | |
|---|---|
| flexural strength according to ISO 178 | 152 N/mm² |
| strain of the outer fibre according to ISO 178 | 6.54% |
| impact strength according to VSM 77105 | 12.3 kJ/m² |
| cold-water absorption after 4 days at 25° C. | 0.35% by weight |
| glass transition temperature | 102° C. |

Aluminum plates bonded with this mixture exhibit, according to DIN 53283, a tensile shearing strength of 16.1N/mm². [ISO = International Standards Organisation; VSM = "Verein Schweizerischer Maschinenindustrieller" (Association of Swiss Machine Manufacturers); DIN = "Deutsche Industrie-Normen" (German Industrial Standards)]

EXAMPLE II 100 parts of resin I, 20.02 parts of 1,2-propylene glycol-monocyanoacetate (compound according to Example 2) and 2.40 parts of N-(4-chlorophenyl)-N',N'-dimethylurea are mixed, cast and cured in the manner described in Example 1. The following properties are determined:

| | |
|---|---|
| flexural strength (ISO 178) | 143 N/mm² |
| strain of the outer fibre (ISO 178) | 5.93% |
| impact strength (VSM 77105) | 25.4 kJ/m² |
| glass transition temperature | 94° C. |
| cold-water absorption after 4 days at 25° C. | 0.32% by weight |

The above mixture gels in 7.67 minutes at 160° C.

EXAMPLE III 100 parts of resin I, 16.5 parts of glycerol-bis-cyanoacetate (compound according to Example 3) and 2.33 parts of N-(4-chlorophenyl)-N'N'-dimethylurea are mixed, cast and cured in the manner described in Example I. The following properties are determined:

| | |
|---|---|
| flexural strength (ISO 178) | 144.6 N/mm² |
| strain of the outer fibre (ISO 178) | 5.42% |
| impact strength (VSM 77105) | 20.1 kJ/m² |
| glass transition temperature | 116.5° C. |
| cold-water absorption after 4 days at 25° C. | 0.355% by weight |
| tensile shearing strength on Anticorodal according to DIN 53283 | 15.8 N/mm². |

EXAMPLE IV 100 parts of resin I, 21 parts of the compound according to Example 4 and 2.42 parts of N-(4-chlorophenyl)-N',N'-dimethylurea are mixed and further processed in the manner described in Example I. The following properties are determined:

| | |
|---|---|
| flexural strength (ISO 178) | 130.3 N/mm² |
| strain of the outer fibre (ISO 178) | 6.13% |
| impact strength (VSM 77105) | 35.1 kJ/m² |
| heat deflection temperature (ISO 175) | 105° C. |
| cold-water absorption after 4 days at 25° C. | 0.34% by weight |
| boiling-water absorption after 1 hour at 100° C. | 0.73% by weight |
| tensile shearing strength on Anticorodal (DIN 53283) | 12.7 N/mm². |

EXAMPLE V 100 parts of resin I, 28.14 parts of the compound according to Example 5 and 2.56 parts of N-(4-chlorophenyl)-N',N'-dimethylurea are mixed and further processed in the manner described in Example I. The following properties are determined:

| | |
|---|---|
| flexural strength (ISO 178) | 152.75 N/mm² |
| strain of the outer fibre (ISO 178) | 5.36% |
| impact strength (VSM 77105) | 32.5 kJ/m² |
| heat deflection temperature (ISO 175) | 75° C. |
| cold-water absorption after 4 days at 25° C. | 0.33% by weight |
| boiling-water absorption after 1 hour at 100° C. | 1.33% by weight |
| tensile shearing strength on Anticorodal (DIN 53283) | 13.4 N/mm². |

EXAMPLES VIa TO VId

These Examples show the curing of bi-reactive mixtures of epoxide resin and isocyanates. The cyanacetyl groups of the curing agent of the formula I react with the epoxide resin, while the hydroxyl groups react mainly with the isocyanate. Accordingly, an —OH-/—NCO ratio of 1 is chosen in each case.

TABLE

| | VIa | VIb | VIc | VId |
|---|---|---|---|---|
| Components (parts) | | | | |
| unmodified epoxide resin based on bisphenol-A with an epoxide-equivalent weight of 190 (5.3 equivalents/kg) | 74.49 | 74.49 | 74.61 | 76.64 |
| compound according to Example 6 | 17.74 | 17.74 | 17.31 | 17.78 |
| tolylene-diisocyanate (80% by wt. of 2,4-derivative and 20% by wt. of 2,6-derivative) | — | 5.76 | — | — |
| 4,4'-diphenylmethane-diisocyanate | — | — | 8.07 | — |
| hexamethylene-diisocyanate | — | — | — | 5.57 |
| N—(4-chlorophenyl)-N',N'—dimethylurea | 1.84 | — | — | — |
| gelling | 8 hours at 120° C. | | | |
| curing | 8 hours at 150° C. | | | |
| properties | | | | |
| flexural strength (ISO 178) (N/mm²) | 153.4 | 130.5 | 149.3 | 150.7 |
| strain of the outer fibre (ISO 178) (%) | 5.9 | 4.0 | 6.1 | 5.4 |
| impact strength (VSM 77105) (kJ/m²) | 18.8 | 14.1 | 22.1 | 25.3 |
| heat deflection temperature (ISO 175) (°C.) | 96 | 117 | 121 | 107 |
| boiling-water absorption, 1 h at 100° C. (% by weight) | 1.01 | 0.77 | 0.72 | 0.88 |

The cured mixtures VIc and VId containing the isocyanates have an impact strength considerably higher than that of the isocyanate-free mixture VIa; the heat deflection temperature values of the isocyanate-containing mixtures VIb, VIc and VId are higher and the water-absorption values thereof lower than the corresponding values in the case of the isocyanate-free mixture VIa.

EXAMPLE VII 100 parts of resin I, 18.9 parts of the compound according to Example 7 and 2.38 parts of N-(4-chlorophenyl)-N',N'-dimethylurea are mixed and further processed in the manner described in Example I. The following properties are determined:

| flexural strength (ISO 178) | 96.28 N/mm² |
|---|---|
| strain of the outer fibre (ISO 178) | 3.45% |
| impact strength (VSM 77105) | 7.6 kJ/m² |
| heat deflection temperature (ISO 175) | 108° C. |
| cold-water absorption after 4 days at 25° C. | 0.36% by weight |
| boiling-water absorption after 1 h at 100° C. | 0.80% by weight |
| tensile shearing strength on Anticorodal (DIN 53283) | 11.15 N/mm². |

The heat deflection temperature is increased to 144° C. by the addition of 16.53 parts of tolylenediisocyanate (80% by weight of the 2,4-derivative and 20% by weight of the 2,6-derivative) to the above mixture.

EXAMPLE VIII 100 parts of resin I, 17.87 parts of the compound according to Example 8 and 2.36 parts of N-(4-chlorophenyl)-N',N'-dimethylurea are mixed and further processed in the manner described in Example I. The following properties are determined:

| flexural strength (ISO 178) | 121.8 N/mm² |
|---|---|
| strain of the outer fibre (ISO 178) | 7.0% |
| impact strength (VSM 77105) | 18.4 kJ/m² |
| heat deflection temperature (ISO 175) | 110° C. |
| cold-water absorption after 4 days at 25° C. | 0.3% by weight |
| boiling-water absorption after 1 h at 100° C. | 0.45% by weight |
| tensile shearing strength on Anticorodal (DIN 53283) | 5.18 N/mm². |

What is claimed is:

1. A curable mixture containing
(a) an epoxide resin having on average more than one epoxy group in the molecule, and
(b) as curing agent for the epoxide resin, a compound of the formula I

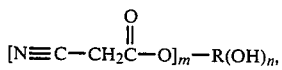

wherein
m and n independently of one another are an integer from 1 to 5, and
m and n together are at most 6, and
R is a radical of the valency m derived from an alcohol having at most 6 hydroxyl groups, which radical can be interrupted by oxygen atoms and has a molecular weight not exceeding 200.

2. A mixture according to claim 1, wherein m and n in the compound of the formula I independently of one another are 1 or 2, and m and n together are 2 to 4.

3. A mixture according to claim 1, which contains as component (b): cyanoacetic acid-2-hydroxyethyl ester, 1,2-propylene glycol-monocyanoacetate, D-mannitol-triscyanoacetate or a compound of the formula

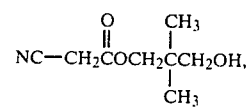

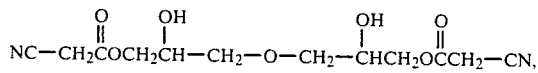

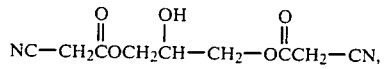

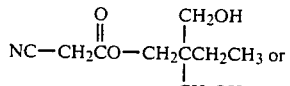

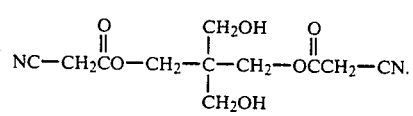

4. A mixture according to claim 1, which contains 1,2-propylene glycol-monocyanoacetate as component (b).

5. A mixture according to claim 1, which contains a liquid epoxide resin as component (a).

6. A mixture according to claim 1, which contains as component (a): an epoxide resin based on bisphenol A, tetrabromobisphenol A or bisphenol F, on phenol-formaldehyde novolaks or cresol-formaldehyde novolaks, on polyhydric aliphatic alcohols or on aromatic mono- or polyamines.

7. A mixture according to claim 1, which contains a liquid unmodified epoxide resin based on bisphenol F or bisphenol A, as component (a).

8. A mixture according to claim 1, which additionally contains 0.1 to 10 parts by weight, relative to 100 parts by weight of epoxide resin (a), of a curing accelerator (c).

9. A mixture according to claim 8, which contains as curing accelerator (c) a compound of the formula II

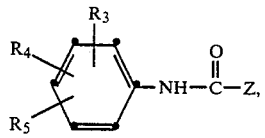

wherein Z is the group

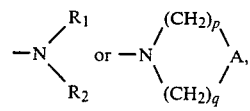

A is —CH₂— or —NH—, p is zero, 1 or 2, q is 1 or 2, R₁ and R₂ independently of one another are each an alkyl group having 1–4 carbon atoms, R₃ and R₄ independently of one another are each hydrogen, halogen, alkyl having 1–4 carbon atoms, alkoxy having 1–4 carbon atoms, phenyl or phenoxy, and R₅ is hydrogen, trifluoromethyl, nitro or one of the groups 10. A mixture according to claim 8, which contains as curing accelerator (c) 0.1 to 5 percent by weight, relative to 100 parts by weight of epoxide resin (a), of N-(4-trifluoromethylphenyl)-N′,N′-dimethylurea, N-(4-chlorophenyl)-N′,N′-dimethylurea or N-(4-ethoxyphenyl)-N′,N′-dimethylurea.

11. A process for producing cured products by heating the mixture according to claim 1 to a temperature of above 120° C.

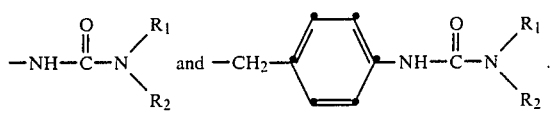

* * * * *